United States Patent
Makdissi

(10) Patent No.: US 8,494,629 B2
(45) Date of Patent: Jul. 23, 2013

(54) APPARATUS AND METHOD FOR AUTOMATIC OPTIMIZATION OF ATRIOVENTRICULAR DELAY FOR AN ACTIVE MEDICAL DEVICE

(75) Inventor: Alaa Makdissi, Paris (FR)

(73) Assignee: Sorin CRM S.A.S. (FR)

( * ) Notice: Subject to any disclaimer, the term of this patent is extended or adjusted under 35 U.S.C. 154(b) by 339 days.

(21) Appl. No.: 13/030,002

(22) Filed: Feb. 17, 2011

(65) Prior Publication Data
US 2011/0202099 A1    Aug. 18, 2011

(30) Foreign Application Priority Data
Feb. 17, 2010 (FR) ...................................... 10 51120

(51) Int. Cl.
*A61N 1/00* (2006.01)
(52) U.S. Cl.
USPC .................................... 607/9; 607/17; 607/27
(58) Field of Classification Search
USPC .................. 607/4–6, 9, 17–18, 23, 25, 27–28
See application file for complete search history.

(56) References Cited

U.S. PATENT DOCUMENTS

| | | | |
|---|---|---|---|
| 5,304,208 A | 4/1994 | Inguaggiato et al. | |
| 5,496,351 A | 3/1996 | Plicchi et al. | |
| 5,693,075 A | 12/1997 | Plicchi et al. | |
| 6,522,923 B1 | 2/2003 | Turcott | |
| 6,792,310 B1 * | 9/2004 | Turcott et al. | 607/27 |
| 7,194,306 B1 * | 3/2007 | Turcott | 607/17 |
| 7,676,264 B1 * | 3/2010 | Pillai et al. | 607/9 |
| 7,894,902 B2 | 2/2011 | Rom | |
| 7,941,218 B2 * | 5/2011 | Sambelashvili et al. | 607/17 |
| 2007/0179542 A1 | 8/2007 | Prakash et al. | |
| 2008/0147130 A1 | 6/2008 | Rom | |
| 2009/0157134 A1 * | 6/2009 | Ziglio et al. | 607/9 |
| 2010/0145402 A1 | 6/2010 | Rom | |
| 2010/0185250 A1 | 7/2010 | Rom | |

FOREIGN PATENT DOCUMENTS

| EP | 0515319 | 12/1992 |
|---|---|---|
| EP | 0655260 | 10/1994 |

(Continued)

OTHER PUBLICATIONS

Foreign Search Report (Annexe Au Rapport De Recherche Preliminaire Relatif A La Demande De Brevet Francais No. FR1051120 FA732555), Aug. 18, 2010.

*Primary Examiner* — Christopher D Koharski
*Assistant Examiner* — Catherine Voorhees
(74) *Attorney, Agent, or Firm* — Foley & Lardner LLP

(57) ABSTRACT

An active medical device such as pacemaker, defibrillator and/or resynchronizer with automatic optimization of atrioventricular delay is disclosed. The active medical device is adapted for analyzing a signal delivered by a hemodynamic sensor such as an endocardial acceleration sensor, whose variation according to the AVD is represented by a sigmoid function. An optimal AVD is searched by: applying a reference AVD (XC), at least one left AVD (XL, XLL) and at least one right AVD (XR, XRR); measuring the corresponding hemodynamic parameters (Y1, Y2, Y3, Y4, Y5); evaluating the second derivative of the function at the respective points (XC, Y3; XL, Y2; XR, Y4) of the characteristic corresponding to the reference AVD, to the left AVD and to the right AVD; estimating from these values of second derivatives, the position of an intermediate point of the characteristic for which the second derivative is zero or minimum, and determining the corresponding AVD for that intermediate point as the optimal AVD.

10 Claims, 3 Drawing Sheets

FOREIGN PATENT DOCUMENTS

| | | |
|---|---|---|
| EP | 2070562 | 6/2009 |
| WO | WO 2006090397 | 2/2006 |
| WO | WO 2006126185 | 5/2006 |
| WO | WO 2008010220 | 1/2008 |

\* cited by examiner

APPARATUS AND METHOD FOR AUTOMATIC OPTIMIZATION OF ATRIOVENTRICULAR DELAY FOR AN ACTIVE MEDICAL DEVICE The present application claims the benefit of French Application No. 10-51120 entitled "Active Implantable Medical Device Such As Pacemaker, Defibrillator and/or Resynchronizer with Automatic Optimization of the Atrioventricular Delay" and filed Feb. 17, 2010, which is hereby incorporated by reference in its entirety.

FIELD

The present invention relates to "active implantable medical devices" as defined by the 20 Jun. 1990 Directive 90/385/EEC of the Council of the European Communities, and more particularly to those devices that continuously monitor a patient's heart rhythm and if necessary deliver to the heart of the patient electrical pulses for stimulation, resynchronization and/or defibrillation in response to detection of a cardiac rhythm disorder.

BACKGROUND

A typical implantable medical device runs a classic "dual chamber" operating mode in which the device monitors the ventricular activity after an atrial event that is either spontaneous (i.e., P wave detection of an atrial depolarization) or stimulated (i.e., application of an A pulse of atrial pacing). After detecting an atrial event, the device starts to count a delay period referred to as "atrio-ventricular delay" (AVD). If no spontaneous ventricular activity (R wave detection of a ventricular depolarization) is detected at the expiry of an AVD, the device triggers stimulation of a ventricle (either left or right ventricle or both) by applying an electrical pulse for ventricular pacing.

The settings of the device are regularly reassessed to adjust stimulation parameters if necessary. The configuration and parameter settings for the stimulation therapy are appropriately modified as the patient's clinical status evolves over time.

The standard technique for adjusting stimulation parameters including the AVD starts with the estimation of the characteristic delays of the systole by echocardiography, especially the delay of opening of the aortic valve. However, this adjustment procedure should be implemented in hospitals and by qualified personnel. The procedure is long and costly, and thus cannot be applied as often as it would be useful or necessary without interfering with the patient's daily life despite the beneficial effects of the stimulation therapy.

A "multisite" implantable device that has more than two stimulation sites makes the echocardiographic assessment even more difficult because it requires testing several successive pacing configurations (e.g., selecting different sites and/or sequencing different stimulation pulses applied to the selected sites), and determining an optimal AVD for each of these configurations. For these reasons, a large number of combinations is tested rendering the procedure lengthy and difficult to manage, thus excluding it from being a routine operation.

These implantable devices ensure a joint and permanent pacing of the left and right ventricles to resynchronize them by a technique known as Cardiac Resynchronization Therapy ("CRT") or Bi-Ventricular Pacing ("BVP"). These particular devices are commonly referred to as CRT pacemakers or CRT devices. In addition to setting an appropriate AVD, these devices optimize a delay called interventricular delay ("VVD"). The VVD is used to separate the respective moments of stimulation of the left and the right ventricles. The VVD is adjusted to resynchronize the contraction of the ventricles with a fine optimization of the patient's hemodynamic status. The search for an optimum pair (or couple) of {AVD, VVD} can therefore be very long, because it requires multiple scans and tests of the AVD for various potential values of VVD.

EP2 070 562 A1 and its counterpart US Patent Publication 2009/0157134 (both assigned to Sorin CRM S.A.S, previously known as ELA Medical) describe a technique for testing a biventricular stimulation device by successive scans a plurality of stimulation configurations.

There remains, however, a need for a technique to evaluate in a simple, rapid, automated, and precise procedure the impact of different stimulation parameters, including the AVD, so as to optimize the patient's hemodynamic status.

One automated method for optimizing the AVD is described in the article by J M Dupuis et al.: *Programming Optimal atrioventricular delay in Dual Chamber Pacing Using Peak endocardial Acceleration: Comparison with a Standard Echocardiographic Procedure*, PACE 2003; 26: [Pt II], 210-213. This technique involves scanning the AVD in a given stimulation configuration and tracing a characteristic value of the peak of endocardial acceleration ("PEA") according to the AVD. The optimal value of the AVD is considered to be the inflection point of the characteristics, i.e., the point corresponding to the maximum duration of ventricular filling without truncating the A wave (i.e., the minimum delay between the closing of the mitral valve and the beginning of the QRS complex).

Although the corresponding algorithm gives satisfactory results, it requires several minutes, especially in case of a multisite device or a CRT device that requires multiple scans of AVD for various values of other parameters that are tested separately (including the VVD) to select an optimal pair of {AVD, VVD}.

Another optimization technique, which is much faster, and thus can be implemented in real time, is described in WO 2006/090397 A2 and WO 2006/126185 A2. The optimization algorithm described therein uses a spike-type neural network to identify the maximum of a hemodynamic function (e.g., stroke volume). The spike neural network, however, requires a dedicated processor, thus redesigning of the device demanding higher power consumption. A software implementation of the optimization algorithm is possible, but it requires extra computing resource that is unattainable in an ultra-low power consumption microcontroller that is adequate for use in an implantable medical device.

WO 2008/010220 describes yet another technique, in which a spike neural processor is combined with a reinforced learning algorithm (e.g., Q-learning), which learns and associates the cardiac conditions of the patient with the optimal delays. The Q-learning algorithm offers improved immunity to noise and increases the speed of convergence in searching optimal parameters. However, in order to achieve the desired performance, additional hardware resource is required, including a microprocessor in addition to the spike neural processor, which incurs extra cost, higher power consumption, and an increase spatial requirement for the implantable device.

OBJECTS AND SUMMARY

It is, therefore, an objective of the present invention to provide a new simple, rapid, automated and reliable technique for optimizing the AVD parameter.

It is further an objective of the present invention to provide such an optimization technique for real time application, with a response time of only a few cardiac cycles, while requiring only simple hardware and software resources to be compatible with a currently available implantable device including a CRT pacemaker.

To this end, one aspect of the present invention is directed to an active medical device of a known type, comprising: an implantable cardiac prosthesis device such as a pacemaker, a CRT pacemaker, a defibrillator and/or a resynchronizer. The active medical device comprises means for detecting atrial and ventricular events, means for stimulating the ventricle(s), and means for applying to the means for stimulating an atrioventricular delay AVD. The AVD is counted from the moment of detection of a spontaneous or paced atrial event. At the end of the AVD, a ventricular pacing is applied in the absence of a corresponding spontaneous ventricular event. The active medical device further comprises a hemodynamic sensor; means for analyzing the signal delivered by the hemodynamic sensor and delivering as a function of the AVD a hemodynamic parameter having a variation that is represented by a sigmoid-type characteristic; and means for seeking an optimal AVD by analyzing the sigmoid-type characteristic.

In one embodiment of the present invention, the means for seeking an optimal AVD preferably operates without scanning of the sigmoid-type characteristic, and more preferably comprises: means for applying a reference AVD (Xc) determined by a current value of the optimal AVD or by a default ADV value, e.g., a predetermined value of AVD, and measuring the corresponding hemodynamic parameter; means for applying at least one left AVD that is less than the reference AVD, and measuring the corresponding hemodynamic parameter; means for applying at least one right AVD that is greater than the reference AVD, and measuring the corresponding hemodynamic parameter; means for evaluating the second derivative value of the function at the respective points of the characteristic corresponding to the reference AVD, the left AVD and the right AVD; means for estimating, from the second derivative values thus obtained, the position of an intermediate point of the characteristic for which the second derivative value is equal to zero or at a minimum; and means for determining the corresponding AVD for that intermediate point as the optimal AVD.

In one embodiment, the value of the reference AVD is selected as either a current value of the optimal AVD or a predetermined AVD value.

In another embodiment, the device in accordance with the present invention comprises: means for applying two left AVDs having two different time intervals, respectively less than the reference AVD; means for applying two right AVDs having two different time intervals, respectively greater than the reference AVD. In this embodiment: the means for estimating the second derivative of the function at the point corresponding to the reference AVD further comprises means operating by a computation of the increments of the function between the left AVD and the right AVD, framing the reference AVD; the means estimating the second derivative of the function at the point corresponding to the left AVD is means operating by computation of the increments between the two left AVDs; and the means for estimating the second derivative of the function at the point corresponding to right AVD is means operating by computation of the increments between the two right AVDs.

In one preferred embodiment, the consecutive values of left AVD, right AVD and reference AVD are separated by equal time steps.

In another embodiment, the means for estimating the position of the intermediate point comprises means for determining an existence of a zero crossing between the second derivative values corresponding to the left AVD and right AVD, and means for, in this case, operating a linear interpolation calculation between the points corresponding to the left AVD and the right AVD.

Preferably, the means for estimating the position of the intermediate point include means for determining an absence of zero crossing between the second derivative values corresponding to the left AVD and to the right AVD, and means for, in this case, select as intermediate point, among the three points corresponding to the reference AVD, to the left AVD and to the right AVD, the one minimizing the second derivative value.

In yet another embodiment, the device preferably includes means for determining the sign of the slope of the function at the characteristic point corresponding to the reference AVD, and means for inhibiting the means for searching for an optimal AVD on detection of a non-compliant slope sign.

In a preferred embodiment, the device further comprises means for analyzing the activity status of the patient and conditioning the execution of the means for searching for an optimal AVD on a detection of a change in the patient activity. Preferably, the means for analyzing the state of activity comprises means for comparing a heart rate mean value over a short-term and a heart rate mean value over a long-term, and means for activating the means for searching for an optimum AVD if the difference between these two heart rate mean values exceeds a predetermined threshold.

In one embodiment, the hemodynamic sensor is an endocardial acceleration EA sensor, and the hemodynamic parameter is a peak value of endocardial acceleration PEA, derived from either or both of the two peaks of acceleration endocardial PEA1 appearing during the ventricular isovolumetric contraction phase and acceleration endocardial PEA2 appearing during the phase of isovolumetric ventricular relaxation.

BRIEF DESCRIPTION OF THE DRAWINGS

Further features, characteristics and advantages of the present invention will become apparent to a person of ordinary skill in the art from the following detailed description of embodiments of the present invention, made with reference to the drawings annexed, in which like reference characters refer to like elements and in which.

DETAILED DESCRIPTION

With reference to FIGS. 1-5, various embodiments of the present invention will now be described.

According to one embodiment, the present technique for optimizing AVD is implemented in a CRT device, i.e., a resynchronizer device that ensures joint and permanent stimulation of the two ventricles, so as to resynchronize them. The present invention is advantageously applied to this type of device to jointly adjust several interdependent parameters including the AVD and VVD delays. However, it should be understood that the present invention is not limited to such CRT devices and can be applied to optimize the value of the AVD at rest or during exercise in "dual chamber" devices and any other device including more complex devices (triple chamber, quadruple chamber, multisite, CRT, . . . ) as well as the defibrillators including pacing capabilities.

As regards its software aspects, the present invention can be implemented by an appropriate programming of the controlling software of a known device, for example, a cardiac pacemaker or a defibrillator/cardioverter, including means for collecting a signal provided by endocardial leads and/or one or more implanted sensors. As regards it hardware aspects, the present invention can be implemented in a device that includes programmable microcontroller and/or microprocessor circuitry to receive, format, process electrical signals collected (detected) by one or more implanted electrodes, and deliver stimulation pulses to these electrodes. It is possible to transmit by telemetry software and store it in a memory of the implantable device to execute the functions of the present invention as described herein. The adaptation of these devices to implement the functions and features of the present invention is believed to be within the abilities of a person of ordinary skill in the art, and therefore will not be described in detail. One suitable type of device to which the present invention may particularly be applied are those of the Reply and Paradym device families produced and marketed by Sorin CRM, Clamart France, formerly known as ELA Medical, Montrouge, France.

General Configuration of the Device

Figure 1:
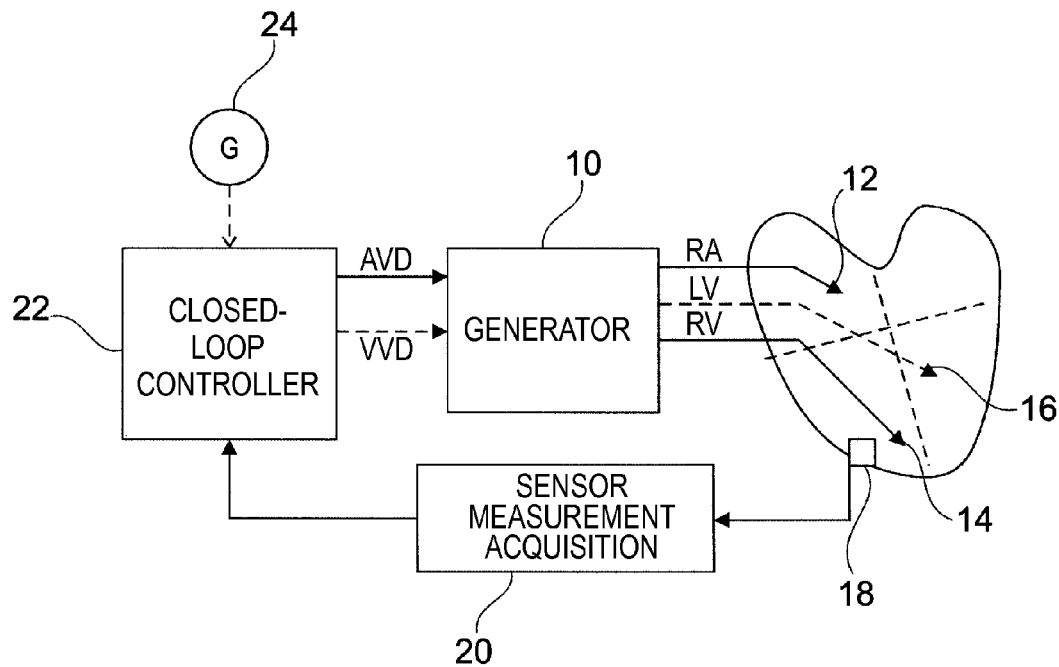
FIG. 1 is a system block diagram of a closed-loop, real-time hemodynamic CRT device, according to one embodiment.

The various elements involved in controlling the AVD (and the VVD, in the case of a CRT device) are illustrated in FIG. 1, in the form of schematic functional blocks. The reference 10 denotes the generator of the device connected to the heart via leads to collect myocardium depolarization signals and to stimulate the myocardium by delivering electrical pulses to the different cavities of the heart. A lead 12 implanted in the right atrium (RA) and a lead 14 implanted in the right ventricle (RV) allow optimizing the atrioventricular delay AVD between the instants of stimulation of the atrium and of the right ventricle for a CRT device. A lead 16 implanted in the vicinity of the left ventricle (LV) in combination with the lead 14 implanted in the right ventricle, allows optimizing the interventricular delay VVD between the left and right ventricles.

The hemodynamic sensor 18 measures hemodynamic signals representing cardiac output from the heart. More specifically, the hemodynamic sensor 18 estimates changes in contractility correlated with increases in blood pressure. Hemodynamic sensors differ from activity sensors (e.g., acceleration sensors) or metabolic sensors (e.g., minute ventilation sensors) that are intended only to diagnose the presence or level of an activity by the patient and to quantify the patient's metabolic needs. Depending on the patient's level of activity or metabolic needs, the stimulation heart rate is adapted. However, the hemodynamic sensor 18 not only monitors the patient's efforts as does an activity sensor or a metabolic sensor, but also provides an indication of the patient's hemodynamic tolerance in relation to certain events, especially the tolerance to a change in the AVD (and VVD, if applicable) parameters by the device.

In a preferred embodiment, the hemodynamic sensor 18 is an endocardial acceleration sensor, called "PEA sensor," having an output representative of the peak of endocardial acceleration. For various descriptions of such a PEA sensor, reference is made to EP 0515319 A1 (assigned to Sorin Biomedica Cardio SpA), which describes how to collect an endocardial acceleration signal (EA signal) using an endocardial lead provided with a distal electrode of stimulation located at the apex of the ventricle and incorporating a micro-accelerometer to measure the endocardial acceleration, and EP 0655260 A1 (assigned to Sorin Biomedica Cardio SpA), which describes a method for processing the signal of measured endocardial acceleration to derive a particular value of the peaks of endocardial acceleration corresponding to the two major noises that are recognizable in each cycle of a healthy heart.

Suitable PEA sensors have been developed by the assignee hereof and commercialized under the brand SonR Fix (trademark) for the family of defibrillators products known by the brand Paradym and Paradym CRT devices.

The present invention also may be implemented in a configuration in which the PEA signal is noninvasively collected by an external sensor, rather than by an implanted sensor, for example, by means of an accelerometer sensor attached to the patient's chest at the sternum.

Whether implanted or external, hemodynamic sensor 18 delivers a signal representing the patient's cardiac output to an acquisition circuit 20. The acquisition circuit 20 is preferably, but not necessarily, incorporated into the generator 10 of the implanted device, but it also may be externally located outside the patient's body.

The acquisition circuit 20 delivers a PEA hemodynamic signal to a controller 22 which forms a closed-loop system. The transmission of a PEA hemodynamic signal can be direct (in case of a sensor 18 and circuit 20 being internal to the device), or be performed by telemetry (in case of an external hemodynamic sensor 18 and a controller 22 incorporated into an implanted device or, conversely, in case of a hemodynamic sensor 18 and an external controller 22 that is integrated in an external programmer used for setting up the generator during a visit to a practitioner).

The controller 22 implements a closed-loop algorithm to derive optimal values of the parameters for controlling the generator, including an optimal AVD, $AVD_{opt}$ (and an optimal VVD for a CRT device). The system may also include (but not necessarily) an auxiliary sensor 24 for measuring a physical parameter, such as an accelerometer or "G Sensor" to detect a beginning or an end of patient's activity.

AVD Optimization Algorithm

The acquisition circuit 20 delivers signals representative of the peak of endocardial acceleration PEA, more precisely, the first peak of endocardial acceleration ("PEA1") that corresponds to the closure of the mitral and tricuspid valves, at the beginning of the ventricular isovolumetric contraction phase (systole). The variations of PEA1 are closely linked to changes in pressure in the ventricle, therefore represent the myocardial contractility. The amplitude of the peak PEA1 is particularly correlated to the positive maximum of the pressure variation dP/dt in the left ventricle.

Figure 2:
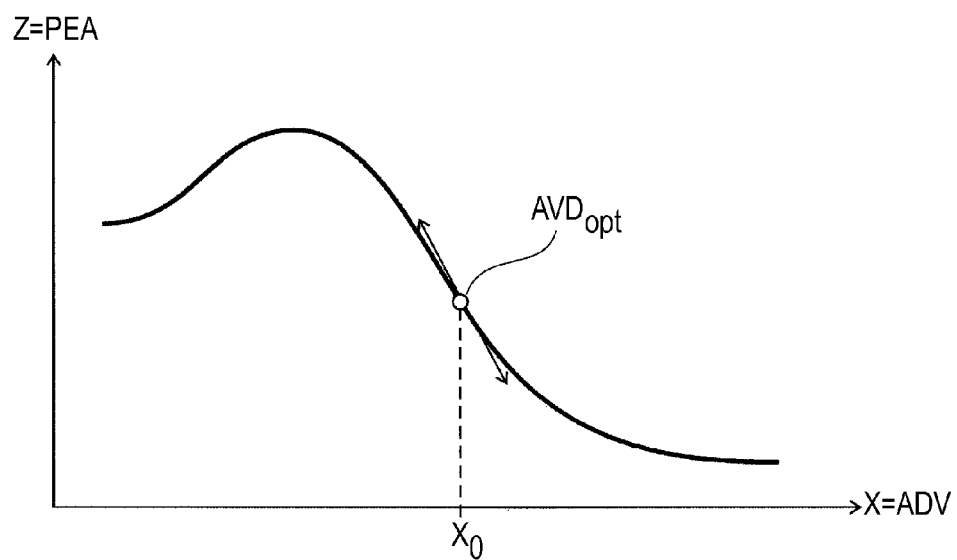
FIG. 2 illustrates exemplary variation of the value of the peak of endocardial acceleration (PEA) obtained from a hemodynamic sensor as a function of the AVD.

The variations of PEA as a function of the AVD follow a relation Z=f(AVD) generally represented by the characteristic curve shown in FIG. 2. The optimum value of the AVD is the point $AVD_{opt}$ located at the inflection point of this characteristic curve. The inflection point corresponds to a maximum duration of ventricular filling without truncation of the A wave (i.e., a minimum delay between the closing of the mitral valve and the beginning of the QRS wave).

In the vicinity of the inflection point representative of an optimal AVD, the characteristic curve can be approximated by a sigmoid function that contains exponential terms: if X denotes the current value of the AVD and $X_0$ denotes the value of an optimal AVD, the shape of the sigmoid curve reflects the variations of the signal representative of PEA in the vicinity of the optimum sought corresponds to a function of the following type:

$$Y = a + b\left(\frac{1}{1 + \exp(c(X - X_0))}\right),$$

in which the parameters a, b, c and $X_0$ are quantities that vary over time and according to the patient's status.

The second derivative at point $X_0$, a point of inflection of the sigmoid curve Y, is equal or is close to zero, and is used as the basis to optimize the AVD.

Figure 3:
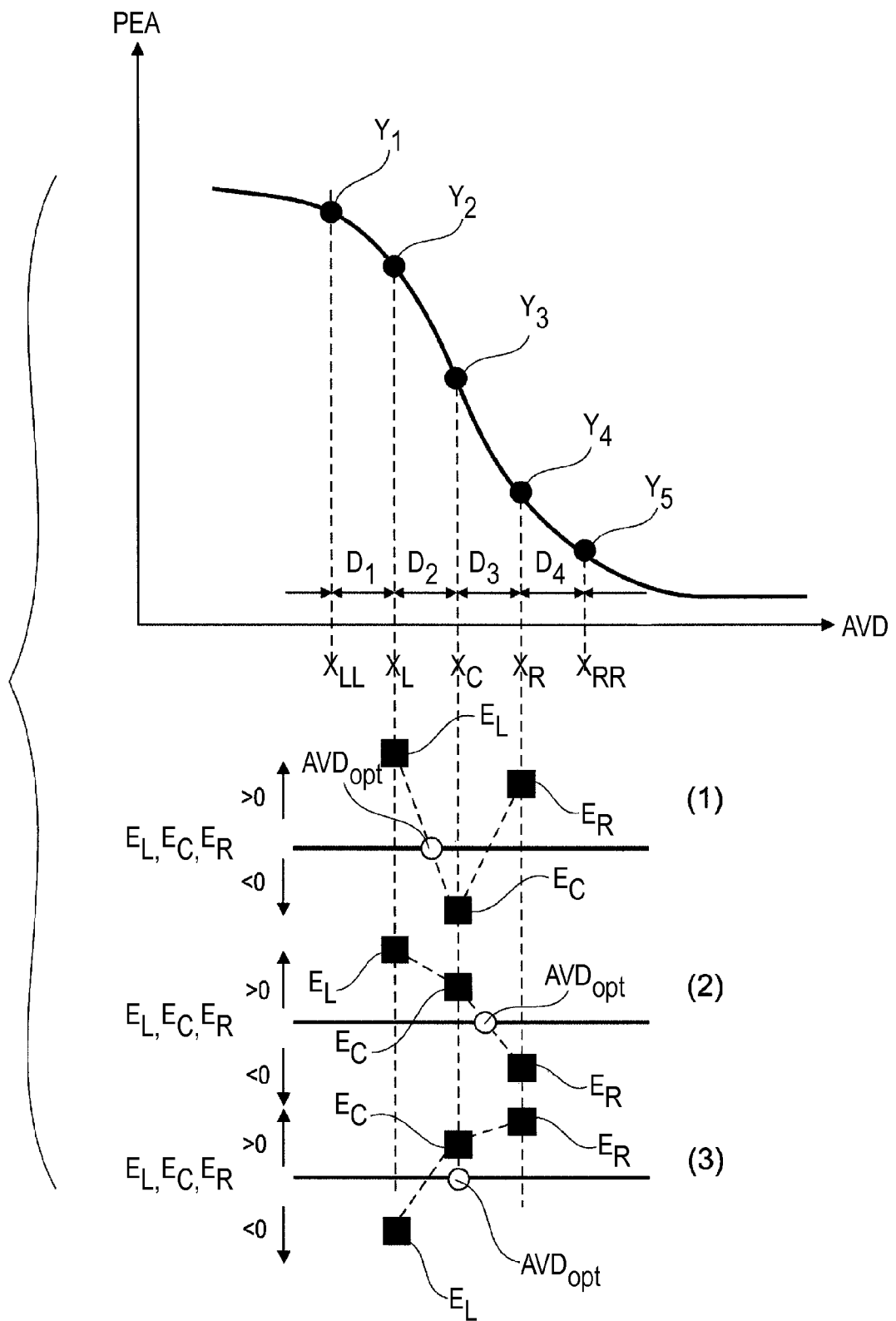
FIG. 3 illustrates measured PEA values in accordance with varying AVD, and a procedure to derive an optimal AVD value.

The details of the optimization algorithm of the present invention will now be further explained with reference to FIG. 3. The optimization algorithm starts with the last optimal value of the AVD, hereinafter designated $X_C$ (i.e., the central value of the current value X of the AVD) and searches for the point at which the second derivative is zero or minimal around this value $X_C$. In the case that no value of optimal AVD is known, especially at the start of the algorithm, a typical mean value may be chosen, for example $X_C$=120 ms.

The algorithm tests several points surrounding delay $X_C$, and from the results of these tests, determines by interpolation or by a search for a minimum, the value of an optimal AVD. In other words, instead of performing continuous scans of the values of the AVD to perform the optimization, tests are performed on only a limited number of discrete values of the AVD. The algorithm directly deduces an optimum position from the results of these tests, regardless of the order of the tests unlike continuous scans that assume a continuous variation of the AVD on a relatively wide range.

In addition to the central point $X_C$ that corresponds to the last known optimal AVD, measurements also are performed for two points $X_L$ and $X_{LL}$ located to the left of $X_C$, and for two points $X_R$ and $X_{RR}$ located on the right of that point $X_C$ of the characteristic. These various points $X_{LL}$, $X_L$, $X_C$, $X_R$ and $X_{RR}$ are separated by corresponding delays $D_1$, $D_2$, $D_3$ and $D_4$. Preferably, the delays $D_1$, $D_2$, $D_3$ and $D_4$ are equal and correspond to the step D for scanning the AVD, for example, D=20 ms. In reference to the central delay $X_C$, the values of the delays $X_L$, $X_R$, $X_{RR}$ and $X_{LL}$ are given by:

$X_L = X_C - D$, (Left AVD)

$X_R = X_C + D$, (Right AVD)

$X_{LL} = X_L - D$ $X_{RR} = X_R + D$

In case variable steps of delays are used, the five points are chosen such that:

$X_L = X_C - D2$ $X_R = X_C + D3$ $X_{LL} = X_L - D1$ $X_{RR} = X_R + D4$ $Y_1$, $Y_2$, $Y_3$, $Y_4$ and $Y_5$ are the five measurements of PEA corresponding to the respective values $X_{LL}$, $X_L$, $X_C$, $X_R$, $X_{RR}$ of the AVD. Each value $Y_1$ to $Y_5$ is preferably obtained by averaging from four to ten measurements of the PEA.

The algorithm then calculates:
the second derivative at the center $E_C$, at the point $(X_C, Y_3)$
the second left derivative $E_L$, at the point $(X_L, Y_2)$, and
the second right derivative $E_R$ at the point $(X_R, Y_4)$,
and the following second derivative values are obtained by:

$E_C = 2*((D_2+D_3)*Y_3 - D_3*Y_2 - D_1*Y_4)/(D_2+D_3)$ $E_L = 2*((D_1+D_2)*Y_2 - D_2*Y_1 - D_1*Y_3)/(D_1+D_2)$ $E_R = 2*((D_3+D_4)*Y_4 - D_3*Y_3 - D_1*Y_5)/(D_3+D_4)$

When the step D is fixed, the calculation is simplified and the second derivative values are obtained by:

$E_C = 2*Y_3 - Y_2 - Y_4$ $E_L = 2*Y_2 - Y_1 - Y_3$ $E_R = 2*Y_4 - Y_3 - Y_5$

It is noted that the values X and Y are digitized sampled values, and the calculation of second derivative is reduced to a simple arithmetic calculation.

Once the three second derivatives $E_L$, $E_C$ and $E_R$ are calculated, the AVD that corresponds to a zero crossing of the second derivative is sought, by applying the three rules (1), (2) and (3) as below:

If $((E_L > 0)$ and $(E_C <= 0))$ then
  Rule (1)
  The zero crossing is calculated by linear interpolation:

$AVD_{opt} = X_L + E_L*(X_C - X_L)/(E_L - E_C)$

Optimum found->End of the algorithm

If $((E_C > 0)$ and $(E_R <= 0))$ then
  Rule (2)
The zero crossing is calculated by linear interpolation:

$AVD_{opt} = X_C + E_C*(X_R - X_C)/(E_C - E_R)$

Optimum found->End of the algorithm

Otherwise
  Rule (3).
  If there is no zero crossing of second derivative between $X_L$ and $X_R$, the optimum is approximated by the point at which the value of the second derivative is minimal (i.e., the nearest value to zero) in absolute value. The determination according to this rule is made by the following steps:
  $AVD_{opt} = X_L$, $E_m = Abs(E_L)$;
  If $(Abs(E_C) < E_m)$ then $ADV_{opt} = X_C$, $E_m = Abs(E_C)$;
  If $(Abs(E_R) < E_m)$ then $ADV_{opt} = X_R$;
  The optimum is approached→End of the algorithm.

At the end of the algorithm, one of three rules was necessarily applied, and the optimal value $AVD_{opt}$ is found to be between $X_L$ and $X_R$.

For security purpose, there may be an additional condition applied to prevent modification of the AVD in case where the PEA measurements cannot be fitted into a decreasing sigmoid characteristic curve in the direction of increasing AVD. In one embodiment, an additional condition of $Y_2 > Y_4$ is applied. This condition is equivalent to testing whether the slope of the curve PEA=f(AVD) around the central point $X_C$ is negative.

Detection of Patient Activity

According to another aspect of the present invention, the optimization algorithm of the AVD is not applied in a continuous manner, but only is applied upon detection of a significant change in the patient's activity. For example, such a significant change in the patient's activity occurs in a detected transition from a rest condition to an exercise condition, or vice versa. The optimization algorithm is applied to adapt or closed-loop control the AVD if a continuous improvement of the patient's hemodynamic status is sought.

Figure 4:
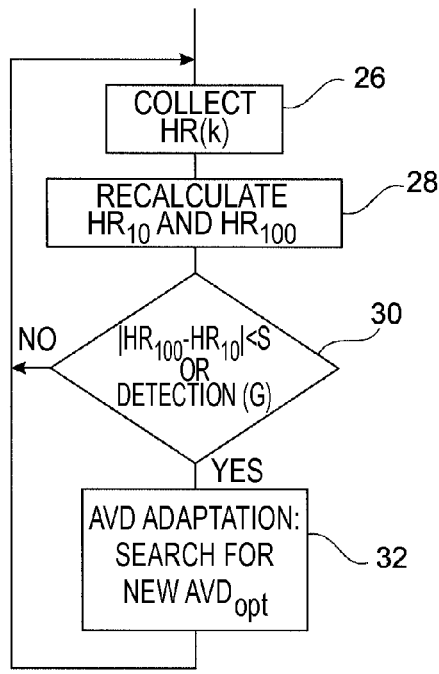
FIG. 4 is a flow chart of an algorithm for detecting a change in a patient's hemodynamic status.

A preferred algorithm adapted for detecting a change in the patient's hemodynamic status by passing from a rest state to an exercise state or vice versa is described with reference to FIGS. 4 and 5. As illustrated in the flowchart of FIG. 4, the heart rate value HR(k) at each cardiac cycle k is constantly collected (block 26). A short-term mean heart rate value $HR_{10}$ and a long-term mean heart rate value $HR_{100}$, respectively determined over the last ten and hundred cardiac cycles, are calculated or updated, using a recursive formula without saving the last 10 or 100 heart rate values in the memory, by:

$$HR_{10} = (1-1/10)HR_{10} + HR(k)/10$$

$$HR_{100} = (1-1/100)*HR_{100} + HR(k)/100$$

The next step (block 30) is to test for a rapid change in the mean heart rate values that is representative of a change in the level of patient's activity. To that purpose, the difference $|HR_{100} - HR_{10}|$ between the mean values $HR_{100}$ and $HR_{10}$ is calculated, and the absolute value of the difference is compared to a threshold S (test 30). If the condition $|HR_{100} - HR_{10}| > S$ is satisfied, then the search algorithm of a new optimum AVD is triggered (block 32).

It is noted that, alternatively or in addition, the threshold test 30 leading to the triggering of the optimization algorithm can be conditioned on another technique for detecting the patient's effort, including using a signal delivered by an accelerometer G (e.g., sensor 24 in FIG. 1).

Figure 5:
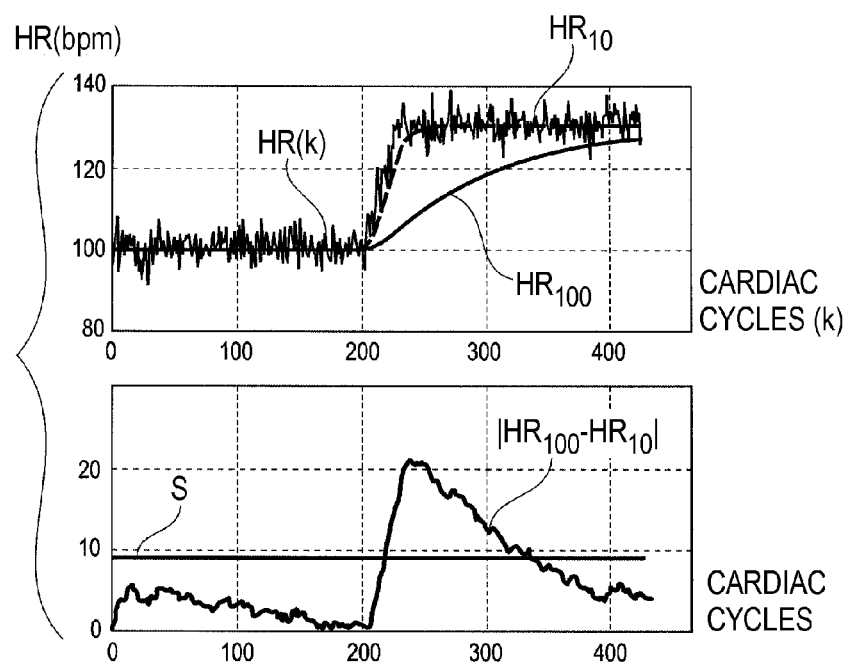
FIG. 5 is a representation of the evolution of a patient's long-term and short-term heart rate mean values during successive cardiac cycles of the heart rate, and the difference between these two mean values compared to an effort state detection threshold.

With reference to FIG. 5, the variations of the three parameters HR (k), $HR_{10}$ and $HR_{100}$ are illustrated over time, with an example of a sudden increase in the level of effort, starting from the patient's cardiac cycle No. 200. This sudden change is detected, as shown in the timing scale at the bottom of FIG. 5, by the crossing of the threshold by the difference $S<|HR_{100}-HR_{10}|$, which triggers an adaptation of the AVD during exercise with a very low delay.

One skilled in the art will appreciate that the present invention may be practiced by other than the embodiments described above, which are presented for purposes of illustration and not of limitation.

The invention claimed is:

1. An active implantable medical device of the pacemaker, defibrillator and/or resynchronizer type, comprising:
   means for detection atrial and ventricular events;
   means for stimulating a ventricle;
   means for applying to the means for stimulating an atrio-ventricular delay AVD, the AVD being counted from the moment of detection of a spontaneous or stimulated atrial event until a pacing of the ventricle is applied in the absence of a detected spontaneous ventricular event;
   a hemodynamic sensor delivering a hemodynamic signal representative of a patient's hemodynamic state;
   means for analyzing the hemodynamic signal and delivering a hemodynamic parameter whose variation with the AVD is a function represented by a sigmoid characteristic; and
   means for searching for an optimal AVD by analyzing the sigmoid characteristic,
   wherein the means for searching for an optimal AVD searches without scanning said sigmoid characteristic, and
   wherein the means for searching for an optimal AVD comprises:
      means for applying a reference AVD ($X_c$) and measuring a corresponding hemodynamic parameter ($Y_3$);
      means for applying at least one left AVD ($X_L$, $X_{LL}$), lower in magnitude than the reference AVD, and measuring a corresponding hemodynamic parameter ($Y_1$, $Y_2$);
      means for applying at least one right AVD ($X_R$, $X_{RR}$), greater in magnitude than the reference AVD, and measuring a corresponding hemodynamic parameter ($Y_4$, $Y_5$);
      means for evaluating the second derivative of said function at the respective points ($X_C$, $Y_3$; $X_L$, $Y_2$; $X_R$, $Y_4$) of the characteristic corresponding to the reference AVD to the left AVD and to the right AVD;
      means for estimating, from the values of the evaluated second derivatives, a position of an intermediate point of the characteristic for which the second derivative has a minimal value; and
      means for determining the corresponding AVD for the intermediate point as the optimal AVD.

2. The device of claim 1, wherein the reference value of the AVD ($X_C$) is selected from a group consisting of said optimal AVD, and a predetermined value of AVD.

3. The device of claim 1, comprising:
   means for applying two left AVD ($X_L$, $X_{LL}$), respectively lower in magnitude than the reference AVD ($X_C$), of two different time intervals; and
   means for applying two right AVD ($X_R$, $X_{RR}$), respectively greater in magnitude than the reference AVD ($X_C$), of two different time intervals,
   wherein the means for estimating the second derivative of the function at the point corresponding to the reference AVD comprises means for computing increments of the function between the left AVD ($X_L$) and the right AVD ($X_R$) framing the reference AVD,
   wherein the means for estimating the second derivative of the function at the point corresponding to the left AVD comprises means for computing increments between the two left AVD ($X_L$, $X_{LL}$), and
   wherein the means for estimating the second derivative of the function at the point corresponding to the right AVD comprises means for computing increments between the two right AVDs ($X_R$, $X_{RR}$).

4. The device of claim 1, wherein the consecutive values ($X_{LL}$, $X_L$, $X_C$, $X_R$, $X_{RR}$) of said left, right and reference AVD are separated by equal temporal steps (D1, D2, D3, D4).

5. The device of claim 1, wherein the means for estimating the position of the intermediate point comprise:
   means for determining an existence of a zero crossing between the second derivative values corresponding to the left AVD and to the right AVD; and means for calculating, in response to the zero crossing, a linear interpolation between the points corresponding to the left AVD and to the right AVD.

6. The device of claim 1, wherein the means for estimating the position of the intermediate point comprise:
   means for determining an absence of a zero crossing between the second derivative values corresponding to the left AVD and to the right AVD; and
   means for selecting, in response to the absence of the zero crossing, as an intermediate point, between the three points corresponding to the reference AVD, to the left AVD and to the right AVD, the one minimizing the value of second derivative.

7. The device of claim 1, further comprising:
   means for determining a sign of the slope of the function at the characteristic point corresponding to the reference AVD, and whether the sign is non-conforming; and
   means for inhibiting the means for searching for optimal AVD in response to a detection of a slope of non-conforming sign.

8. The device of claim 1, further comprising means for analyzing an activity status of the patient, and initiating a search for an optimal AVD in response to a detection of a change of the patient's activity.

9. The device of claim 8, wherein the means for analyzing the patient activity status comprises means for comparing a short-term heart rate average ($HR_{10}$) and a long-term heart rate average ($HR_{100}$) and initiating the means for searching for an optimal AVD when the difference between these two heart rate averages is bigger than a predetermined threshold (S).

10. The device of claim 1, wherein the hemodynamic sensor comprises an endocardial acceleration sensor (EA), and the hemodynamic parameter is a peak of endocardial acceleration value (PEA), derived from at least one of the endocardial acceleration peak (PEA1) appearing during the isovolumetric ventricular contraction phase and the endocardial acceleration peak (PEA2) appearing during the isovolumetric ventricular relaxation phase.

* * * * *